(12) United States Patent
Ribbing et al.

(10) Patent No.: US 7,864,917 B2
(45) Date of Patent: Jan. 4, 2011

(54) IMAGING APPARATUS USING DISTRIBUTED X-RAY SOUCES AND METHOD THEREOF

(75) Inventors: Carolina Ribbing, Aachen (DE); Peter Klaus Bachmann, Würselen (DE); Matthijs Adriaansz, Eindhoven (NL); Han Kroon, Gemert (NL); Herman Stegehuis, Best (NL); Hans Nikol, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 89 days.

(21) Appl. No.: 12/162,692

(22) PCT Filed: Jan. 23, 2007

(86) PCT No.: PCT/IB2007/050229

§ 371 (c)(1),
(2), (4) Date: Jul. 30, 2008

(87) PCT Pub. No.: WO2007/088497

PCT Pub. Date: Aug. 9, 2007

(65) Prior Publication Data

US 2009/0052615 A1    Feb. 26, 2009

(30) Foreign Application Priority Data

Feb. 2, 2006    (EP) .................................. 06101175

(51) Int. Cl.
*H05G 1/60* (2006.01)
*G01N 23/087* (2006.01)
*A61B 6/03* (2006.01)

(52) U.S. Cl. ................................ 378/9; 378/10; 378/16; 378/57; 378/98.9; 378/122

(58) Field of Classification Search ..................... 378/5, 378/9, 10, 16, 57, 98.9, 98.11, 122
See application file for complete search history.

(56) References Cited

U.S. PATENT DOCUMENTS

| 6,236,709 B1 * | 5/2001 | Perry et al. ................... 378/57 |
| 6,333,968 B1 * | 12/2001 | Whitlock et al. ............ 378/136 |
| 6,385,292 B1 * | 5/2002 | Dunham et al. ............. 378/122 |
| 6,449,331 B1 * | 9/2002 | Nutt et al. ..................... 378/19 |
| 6,553,096 B1 * | 4/2003 | Zhou et al. .................. 378/122 |
| 6,674,837 B1 * | 1/2004 | Taskar et al. ................ 378/122 |

(Continued)

FOREIGN PATENT DOCUMENTS

WO    WO0156451 A2    8/2001

(Continued)

OTHER PUBLICATIONS

Zhang et al: "Stationary Scanning X-Ray Source Based on Carbon Nanotube Field Emitters"; Applied Physics Letters, vol. 86, Vo. 18, Apr. 29, 2005,, pp. 184104-1-184104-3.

*Primary Examiner*—Allen C. Ho (57) ABSTRACT

An imaging apparatus includes a multi-dimensional assembly supporting a plurality of x-ray sources that are individually addressable. The plurality of x-ray sources is further configurable to simultaneously emit x-ray spectra at different mean energies. Furthermore, the multi-dimensional assembly includes a plurality of x-ray detectors that are arranged to detect at least a part of the x-rays that are emitted from at least one of the x-ray sources.

18 Claims, 4 Drawing Sheets

U.S. PATENT DOCUMENTS

| | | | |
|---|---|---|---|
| 6,731,716 B2 * | 5/2004 | Mihara et al. | 378/9 |
| 6,760,407 B2 * | 7/2004 | Price et al. | 378/122 |
| 6,876,724 B2 * | 4/2005 | Zhou et al. | 378/122 |
| 7,082,182 B2 * | 7/2006 | Zhou et al. | 378/10 |
| 7,085,351 B2 * | 8/2006 | Lu et al. | 378/122 |
| 7,103,137 B2 * | 9/2006 | Seppi et al. | 378/9 |
| 7,177,391 B2 * | 2/2007 | Chapin et al. | 378/57 |
| 7,192,031 B2 * | 3/2007 | Dunham et al. | 278/122 |
| 7,280,631 B2 * | 10/2007 | De Man et al. | 378/10 |
| 7,295,651 B2 * | 11/2007 | Delgado et al. | 378/92 |
| 7,333,587 B2 * | 2/2008 | De Man et al. | 378/9 |
| 7,606,348 B2 * | 10/2009 | Foland et al. | 378/57 |
| 7,606,349 B2 * | 10/2009 | Oreper et al. | 378/98.9 |
| 7,616,731 B2 * | 11/2009 | Pack et al. | 378/10 |
| 7,627,087 B2 * | 12/2009 | Zou et al. | 378/122 |
| 2004/0109529 A1 | 6/2004 | Eberhard et al. | |
| 2004/0114721 A1 | 6/2004 | Qiu et al. | |
| 2004/0213378 A1 | 10/2004 | Zhou et al. | |
| 2004/0240603 A1 | 12/2004 | Cai et al. | |
| 2004/0240616 A1 | 12/2004 | Qiu et al. | |

FOREIGN PATENT DOCUMENTS

| | | |
|---|---|---|
| WO | WO0184585 A1 | 11/2001 |
| WO | WO03063195 A1 | 7/2003 |

* cited by examiner

IMAGING APPARATUS USING DISTRIBUTED X-RAY SOUCES AND METHOD THEREOF

The invention relates to an x-ray imaging apparatus. The invention further relates to a combined modality imaging. The invention further relates to a method of operation of an imaging system.

X-rays are forms of electromagnetic radiation that typically have a wavelength that is shorter than ultraviolet radiation but longer than gamma radiation. In other words, the x-ray wavelength ranges from about 10 picometer to about 1 nanometer. X-rays find application in medical imaging as well as industrial imaging. In the medical world, x-rays are invaluable for diagnosis, for example in the detection of fractures in bones. With advancements in x-ray technology, today the x-rays are being employed for generating 3D images of a variety of organs, such as by using computed tomography methods. In the industrial world, x-ray scanners are often used to detect flaws in any kind of equipment (tubes, PC boards, chips etc).

An x-ray imaging system used in medical imaging typically consists of an x-ray source, an x-ray detector, a patient table, and means for regulating the duration of exposure, the energy of the emitted x-rays, etc. X-ray imaging systems have evolved into more specific imaging modalities, such as computed tomography (CT) imaging systems which have further evolved to form the current generation of multi-slice CT systems.

An embodiment of such an imaging apparatus is known from prior art document U.S. Patent Application Publication No. 2004/0213378 A1. The document discloses a computed tomography device comprising an x-ray source and an x-ray detecting unit. The x-ray source comprises a cathode, an anode target and a collimator. The cathode comprises a plurality of individually programmable electron emitting units that emit electrons upon an application of an electric field. The anode target emits x-rays upon impact by the emitted electrons. The document further discloses that the electron field emitting unit includes an electron field emitting material and that the electron field emitting material includes a nanostructured material or a plurality of nanotubes or a plurality of nanowires. The use of x-rays in computed tomography methods is also disclosed.

The technique disclosed in the document results in variable absorption of the x-rays at various spots of the object that leads to a lack of resolution in the generated image. This is because e.g. at some spots, where the absorption is extra high, or the imaged object is extra thick, the image becomes grainier. During imaging, the generated 3D image lacks sufficient detail to arrive at an accurate diagnosis. In most of the cases, this causes generation of a fuzzy image making a proper diagnosis difficult.

It is, therefore, an object is to provide an imaging apparatus that generates an image with an improved resolution.

In accordance with a first aspect, an imaging apparatus is disclosed. The imaging apparatus comprises a multi-dimensional assembly that further comprises a plurality of x-ray sources that are individually addressable. The plurality of x-ray sources is further configurable to simultaneously emit x-ray spectra at different mean energies. Furthermore, the multi-dimensional assembly further comprises a plurality of x-ray detectors that are arranged to detect at least a part of the x-rays that are emitted from at least one of the x-ray sources. The plurality of x-ray sources and the plurality of x-ray detectors are distributed on the multi-dimensional assembly. In the discussions that follow, the term x-ray spectra may be interchangeably used with the term x-ray and should not be considered as limiting.

The multi-dimensional assembly, as the name suggests, is typically a structure that is arranged to hold the plurality of x-ray sources and the plurality of x-ray detectors in a desired arrangement. The plurality of x-ray sources and the plurality of x-ray detectors are placed such that at least one x-ray detector from the plurality of x-ray detectors is arranged to detect at least a part of the x-rays emitted by at least one x-ray source from the plurality of x-ray sources.

X-rays are produced as characteristic radiation and as "Bremsstrahlung", which is a term in the German language for braking radiation. It is called braking radiation because x-rays are produced on account of deceleration of electrons when they strike the target. The energy emitted by an accelerated/decelerated particle is proportional to $1/m^2$, with m the rest mass of the particle; Bremsstrahlung therefore plays a particularly important role for light particles and contributes substantially to energy loss in matter for electrons.

By having a different anode material in each of the x-ray sources, characteristic x-ray radiation of different energies may be generated. By adapting certain shapes in arranging or switching the cold emitters on a carrier, the shape of the x-ray beam can be modeled according to special needs, e.g. as defined by the shape of the object to be x-rayed. In a certain implementation, x-rays of different energies can be generated by having one or more groups of x-ray sources, each having a different anode material, activated. In certain other implementations, by changing the acceleration voltage individually, group-wise or for all simultaneously of the x-ray sources, x-ray spectra of variable mean energy may be generated from each x-ray source.

In certain other implementations, it is also possible to have a group of anode materials deposited on a single anode, each anode material arranged to generate x-rays upon impact by electrons. The anode may be of reflection or of transmission type.

By generating x-rays at different mean energies via the plurality of x-ray sources, it is possible to get desired transmission of the x-rays and subsequently better detection of x-rays by at least one x-ray detector from the plurality of x-ray detectors. This allows for a better acquisition of proper image signals to aid in the generation of an image having a high resolution. Different mean x-ray energies may be advantageously used to image various parts of a non-homogeneous object to be examined and to discriminate between different kinds of tissue/material. Multiple energies can be effectively used to achieve a good discrimination between different parts or portions in an object. For example, in medical imaging, the present technique can provide a good discrimination between a contrast agent versus tissue or soft tissue; cartilage versus bone etc.

In a further embodiment, the imaging apparatus comprises an arrangement wherein the plurality of x-ray sources and the plurality of x-ray detectors are stationary. An advantage of an imaging apparatus having the embodied arrangement is that design of the imaging apparatus is simplified with the elimination of moving parts for at least the plurality of x-ray sources and the plurality of x-ray detectors. Other advantages include reduced acoustic noise, reduced mechanical vibrations, reduced power consumption, and reduced cost.

In a further embodiment, the imaging apparatus comprises an arrangement where the plurality of x-ray sources are distributed amongst the plurality of x-ray detectors on a surface of the multi-dimensional assembly. In other words, there is an inter-leaving of the x-ray sources and the x-ray detectors. This allows the plurality of x-ray sources to emit x-rays from different directions and onto the object and also further allows the detection of at least a part of the x-rays in their emitted paths. In certain implementations when the multi-dimensional assembly has multiple surfaces, the currently embodied arrangement may be implemented on more than one surface. An advantage of the invention as embodied herein is that even with stationary x-ray sources and x-ray detectors, and stationary object, generation of a three-dimensional image of the object is possible.

In a further embodiment, the imaging apparatus comprises an arrangement of the plurality of x-ray sources and the plurality of x-ray detectors such that the x-ray sources are grouped together on at least a first surface of the multi-dimensional assembly and the x-ray detectors are grouped together and situated on at least a second surface of the multi-dimensional assembly. In other words, the x-ray sources and the x-ray detectors are situated away from each other. In a certain implementation, the x-ray sources may be grouped on more than one surface, for example when the multi-dimensional assembly is a multi-sided structure such as a box. Similarly, the plurality of x-ray detectors may be grouped and placed on more than one surface. Furthermore, in certain other implementations, a first set of the plurality of x-ray sources and x-ray detectors may be situated on opposite surfaces of the multi-dimensional assembly. In a further embodiment of the current implementation, a different set of x-ray sources and x-ray detectors may be placed at an angle to the first set of x-ray sources and x-ray detectors. This is in contrast to the arrangement embodied previously where the plurality of x-ray sources was distributed amongst the plurality of x-ray detectors. The current arrangement of the invention has an advantage that it facilitates ease of manufacture of the plurality of x-ray sources and the plurality of x-ray detectors as an array.

In a further embodiment, each of the x-ray sources from the plurality of x-ray sources comprises a cold cathode x-ray source. Each individual x-ray source from the plurality of x-ray sources can comprise a cold cathode device that includes a single cathode and a single anode element. The cold cathode device may advantageously be used to avoid the use of a thermal emitter to reduce the size and weight of the x-ray source, reduce power consumption, to facilitate miniaturization and/or to allow the inclusion of a higher number of x-ray sources in a given area. Individual addressing of each of the x-ray sources in the plurality of x-ray sources may typically be achieved by applying a voltage greater than a field emission threshold at each crossing point of a particular row and column, a particular x-ray source may be activated for emission of x-rays.

Cold cathodes give advantages like higher resolution, longer x-ray source lifetime, faster pulsed operation (gating), less power consumption and instant-on behavior. Cooling requirements are less stringent which results in lower set-up and operation costs and freedom of design. An important advantage of using cold cathodes is that instant emission of x-rays is possible, with the x-ray emission beginning the instant an extraction field is applied between the cold cathode and a target anode in the x-ray source. This facilitates faster imaging. Other advantages of using cold cathode x-ray sources include potential miniaturization of the imaging apparatus.

In a further embodiment, the cold cathode x-ray source comprises carbon nanotubes (CNTs). The CNTs are good field emitters or so-called cold cathodes. Advantages of using cold cathodes include lesser power consumption, greater robustness and faster switch on when compared to thermionic electron sources. Alternately, the cold cathode may comprise one of carbon tip (which also includes diamond tip), carbon composite tip, metal tip, semiconductor tip, a ferroelectric material, a pyroelectric material or combinations of the same. In certain other implementations, the cold cathode may also comprise structures that structurally resemble the carbon but essentially be made out of a non-carbon or amorphous material, for example silicon or molybdenum. In such an implementation, the cold cathode can comprise silicon tips or molybdenum tips. In yet another implementation, it is also possible that the cold cathode comprises essentially carbon material as the anode, but comprising a cathode that is made of essentially non-carbon material. Such implementations should be construed as being within the scope of the invention as described herein.

In a further embodiment, the imaging apparatus is arranged to image an object at rest when the imaging apparatus is in operation wherein the object is positioned to receive x-rays from at least one x-ray source. An advantage of the embodied arrangement is that with the object arranged to be at rest, mechanical issues associated with design of the imaging apparatus are reduced. For example, in case of a patient required to undergo imaging and when the patient is kept stationary during the entire imaging process, the patient undergoes little or no stress to cause any erroneous indication of an abnormality like higher blood pressure, higher heart rate, or higher adrenaline levels. Furthermore, a stationary imaging setup facilitates the elimination of artifacts that are attributed to movement of either the imaging apparatus or the patient. One advantage of the embodied arrangement is that while there are no moving parts, the imaging apparatus facilitates the generation of 3D images. This is typically achieved by reconstruction of two or more images taken using multiple x-ray sources and x-ray detectors.

Advantageously, the object is placed such that the plurality of x-ray sources and the plurality of x-ray detectors are disposed around the object, and where each of the x-ray sources in the plurality of x-ray sources is arranged to emit x-rays on the object, and at least one x-ray detector from the plurality of x-ray detectors is arranged to detect at least a portion of the x-rays emitted by at least one x-ray source and transmitted through the object.

It is a further object to provide an imaging apparatus that generates an image with structural as well as functional information content. In order to achieve this object, the combined modality imaging system comprises a first imaging system and a second imaging system. The first imaging system facilitates structural imaging: whereas; the second imaging system facilitates functional imaging. Furthermore, the first and the second imaging systems are arranged to image an object simultaneously or separately and to generate their respective images. This combined modality imaging system is particularly useful when time sensitive imaging or functional imaging needs to be carried out and different parameters need to be measured and monitored. For example, in an imaging procedure, such as mammography, it would be beneficial to include a functional imaging technique (for example, optical imaging or PET imaging or magnetic resonance (MR) imaging) in addition to the structural imaging (x-ray imaging) in order to better understand and provide a more accurate diagnosis about the presence or absence of e.g. a tumor or microcalcification. By performing the imaging simultaneously, problems associated with image co-registration can be avoided.

In a further embodiment, the second imaging system comprises an optical imaging system, a positron emission tomography (PET) system, a single positron emission computed tomography (SPECT) system, an MR imaging system, a thermal imaging system or an ultrasound system. In certain exemplary embodiments, the second imaging system may also comprise a combination of one or more of the specified imaging systems. For example, in the combined modality imaging system the cold cathode-based x-ray sources and corresponding x-ray detectors may be interlaced with a different type of source and detector required for the second imaging system in any pattern conceivable. For instance, every other x-ray source could be replaced with an LED or a laser and correspondingly every other x-ray detector could be replaced with an optical detector.

It is a further object to provide a method of operation of an imaging system. The method comprises configuring a plurality of x-ray sources in a manner such that each x-ray source can emit x-rays at a different energy. The method further comprises detecting at least a part of the x-rays emitted from the plurality of x-ray sources via at least one x-ray detector. The different energies of x-rays may be produced in the manner as described previously in the sections herein above. An advantage of such an arrangement is to obtain higher contrast and/or resolution of images generated from the imaging system. In other words, in an exemplary implementation of the present technique, it is advantageous to optimize the absorption of x-rays in different regions based on knowledge of local absorption of x-rays of the object. Such knowledge typically comes from data stored from previously performed imaging procedures on a similar object and similar regions. Moreover, such knowledge can be obtained dynamically from the same imaging procedure by means of using a previously generated image and subsequently altering the x-ray energy incident on regions that absorb more radiation.

Higher mAs (indicative of the number of x-ray photons generated) are needed in regions where the x-ray absorption is higher and vice versa. Analysis of the previous image and control of mAs for the next image may be performed on the imaging workstation. An advantage of varying the number of x-ray photons is that there is a significant increase in the signal to noise ratio of any 3D image generated by the use of the embodied technique, while the dose to the imaged object is minimized.

In a further embodiment, the method of operation further comprises receiving an object to be imaged between at least one x-ray source from the plurality of x-ray sources and the at least one x-ray detector. This facilitates the emitted x-rays to pass through the object and for at least a part of the x-ray to be received by the detector. The object once received is arranged to be generally stationary. Advantages of the object being stationary have been discussed previously.

In a further embodiment, the method of operation comprises generating a visualization of the object based on at least the part of the x-rays detected by the at least one x-ray detector.

In a further embodiment, the method of operation comprises configuring the plurality of x-ray sources to emit x-rays for a desired duration of time. This duration may be controlled by activating each of the x-ray sources in a desired sequence. This desired sequence may be a serial activation, a parallel activation, or activating only a part of the x-ray sources for x-ray emission. Advantages of the present embodiment are that it minimizes the dose to the object, it facilitates the extraction of image data of a particular region by increasing the signal to noise ratio of the image signal by eliminating the detection of scattered x-rays from a few or rest of the x-ray sources. Conversely, the contribution of scattered radiation may be evaluated in the same way, and the set-up may also open up improved possibilities for incoherent scatter imaging and multi-modality set-ups using e.g. transmission and scatter tomography. In yet another possible embodiment, the method of operation comprises altering projection angles of one or more x-ray sources from the plurality of the x-ray sources based on the visualization.

These and other aspects of the invention will be apparent from and elucidated with reference to the embodiments described hereinafter as illustrated by the following figures, wherein.

Figure 1:
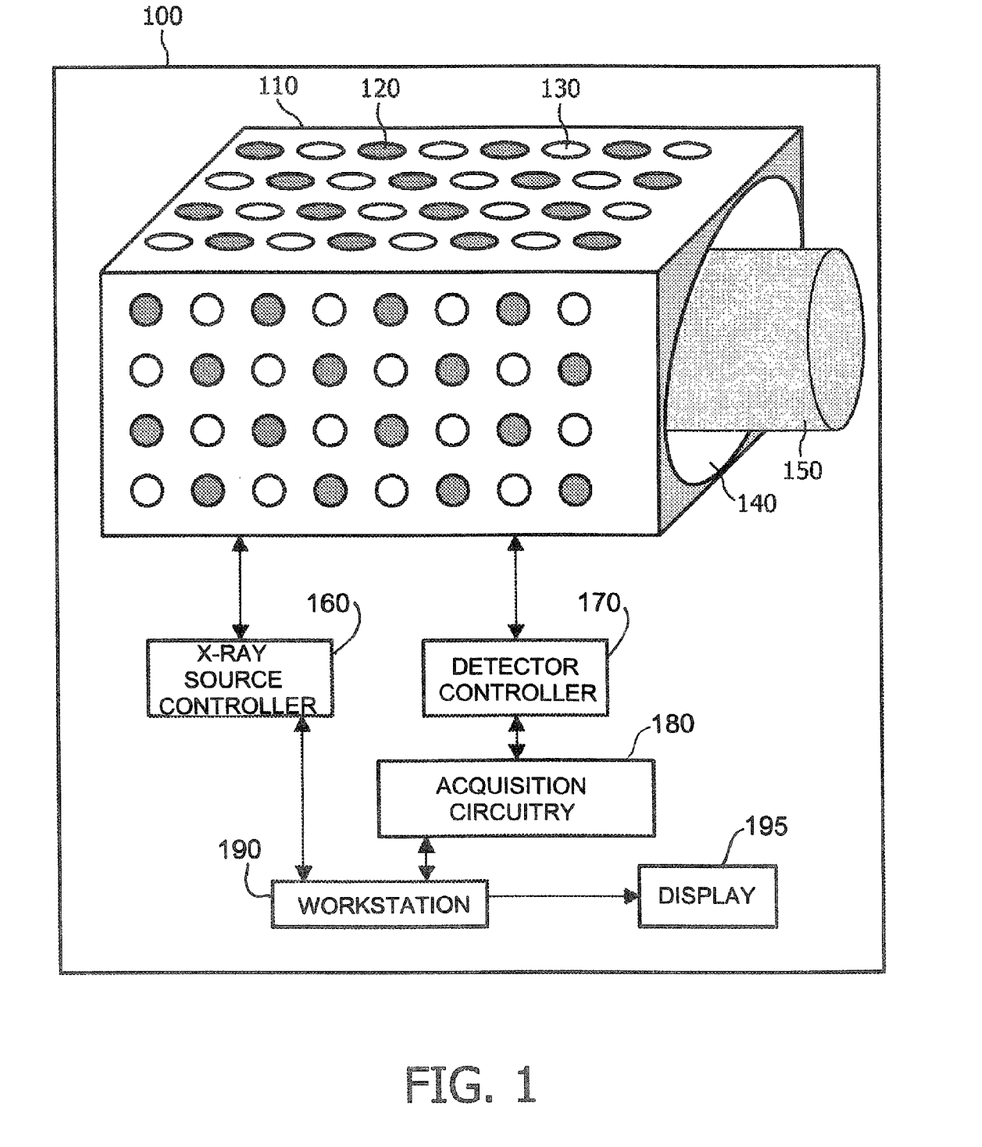
FIG. 1 is a diagrammatical illustration of an exemplary arrangement of an imaging system depicting a plurality of x-ray sources and a plurality of x-ray detectors on a multi-dimensional assembly.

Turning now to the drawings and referring first to FIG. 1, an exemplary imaging apparatus 100 in accordance with one aspect is illustrated. The imaging apparatus 100 includes a multi-dimensional assembly 110. The multi-dimensional assembly 110 comprises a plurality of x-ray sources (generally represented by reference numeral 120) distributed amongst a plurality of x-ray detectors (generally represented by reference numeral 130).

The multi-dimensional assembly 110 typically has an opening 140 through which an object 150 that is required to undergo an imaging procedure may be placed. The object 150 could be of varied type depending on the area of application of the embodied techniques. For instance, in industrial imaging procedures, the object could be anything from printed circuit boards, to unidentified baggage to freight; whereas in medical imaging procedures the object 150 could be a whole patient or a portion of a peripheral body part such as hand, arm, leg, ear, nose, breast, etc. The application of the embodied technique can be in the field of industrial as well as medical imaging with suitable modifications. However, in the sections herein below, in order to provide a better understanding, the description is more in terms of the use in medical imaging.

Returning back to the discussion on FIG. 1, the imaging system 100 further comprises an x-ray source controller 160, an x-ray detector controller 170, a detector acquisition circuitry 180, and an imaging workstation 190. Depending on the task at hand the x-ray controller can perform different acquisition strategies. The imaging workstation 190 will analyze the acquired image signals and generate an optimal visual representation on display 195 and adapt the control strategy of the x-ray source controller 160 and the x-ray detector controller 170 to optimize the information on the display at the minimum x-ray dose level. For example, in a medical imaging procedure, the imaging workstation 190 can facilitate in the automatic selection of optimal projection angle for the x-rays emanating from the x-ray sources while an interventionalist maneuvers a catheter through torqued vessels. The imaging workstation 190 can also facilitate automatic adaptation of x-ray dose by varying the number of electrons that strike the anode of the x-ray source(s) to particular areas of interest in the image, for instance around the catheter tip.

The output of the imaging system 100 is an image that has been composed using these unique characteristics of the imaging system 100. The image may be a three dimensional image having a high resolution and contrast, an image which is decomposed in different materials that constitutes the object or a plain image taken from the optimal viewing angle for a certain predefined task, such as maneuvering a catheter through a tortuous vessel in a patient. Also, it may be a combination of the above (optimal view plane from a 3D material decomposed volume). The high resolution and/or the decomposition is achieved on account of emission of x-rays having different energies from the plurality of x-ray sources 120 as described herein. It may be noted that by imaging an object, it is typically meant to represent imaging over a region of interest on the object in order to generate an image of an internal region within the object. However, in certain other instances, the technique may be employed to directly generate an image of the entire object itself showing both the internal and external representations.

While in the present embodiment, the multi-dimensional assembly 110 is shown to have one opening 140, it should be noted that in certain other implementations, the multi-dimensional assembly 110 may include more than one opening. In certain other implementations, the multi-dimensional assembly 100 may be of a collapsible type, where the multi-dimensional assembly 110 has the plurality of x-ray sources 120 and the plurality of x-ray detectors 130 wrapped around the object 150. In essence, the multi-dimensional assembly 110 would be designed to achieve a desired fit around the object that is to be imaged. Such modifications to the multi-dimensional assembly 110 should be considered to be within the scope of the invention as described herein.

As already explained, each of the plurality of x-ray sources 120 can comprise a cold cathode x-ray source. The advantages of using cold cathode x-ray sources in the invention include reduced power consumption, instant emission of x-rays, high possible switching frequencies, ease of design, and little heat dissipation. Each of the cold cathode x-ray sources includes a single cathode and a single anode. The energy of x-rays emitted by each of the x-ray sources 120 may be controlled in a variety of ways.

In one exemplary implementation, the anode in each x-ray source may have a different material. When electrons strike the anode material upon activation, depending on the anode material, x-rays of a particular energy may be emitted, so called characteristic radiation, together with a background of Bremsstrahlung. Different arrangements of filters or lenses may be used to achieve quasi-monochromaticity of the emitted radiation in cases where this is desired.

In a further exemplary implementation, the anode in each of the x-ray sources 120 may comprise a plurality of anode materials, each located on a specific location on the anode. By configuring the electrons emitted from the cathode to selectively impinge upon a particular area of the anode, x-rays of different energies may be emitted from a single x-ray source. In further embodiments of the implementation, it is also possible to have a plurality of cathodes in lieu of the single large cathode and a single anode having a plurality of one or more anode materials. It should be noted that the plurality of x-ray sources 120 may emit x-rays at different energies but at the same instance of time. As specified previously, an advantage of having each x-ray source or some of the x-ray sources to emit x-rays at a desired energy is that desired levels of x-ray transmission in different regions of the object 150 being imaged may be achieved. As will be appreciated by a person skilled in the art, achieving different penetration depths of x-rays as desired will enable the generation of an image that has a high resolution and contrast even when the object may be exhibiting different x-ray absorption levels or various thickness. Importantly, this also leads to a reduced x-ray dosage to the object 150.

In yet another exemplary implementation, bremsstrahlung spectra of different energies may also be produced by altering the acceleration voltage that enables the electrons to travel at a different velocity before striking the anode target. This is the important way of getting different energies (in comparison to different anode materials), I think. This is because the bremsstrahlung represents most of the x-ray power while the characteristic (quasi-monochromatic) radiation constitutes only a smaller part.

Moreover, it should be noted that with the present geometry of the setup of the x-ray sources and the x-ray detectors, it is possible to carry out an entire imaging procedure without any movement of the object 150 after it has been placed in the multi-dimensional assembly 110. This may be achieved by selectively activating each of or groups of the plurality of x-ray sources 120 in a desired sequence and desired duration of time. In certain instances, one or some of the x-ray sources 120 may be activated for a particular duration of time and the attenuated primary x-rays from the activated x-ray sources and that which passes through the object 150 may be detected by one or more of the x-ray detectors 130.

The x-ray source controller 160 is adapted to control the plurality of x-ray sources 120. The plurality of x-ray sources 120 may be activated one at a time, a few at a time or all at the same time. The x-ray source controller 160 is adapted to address each x-ray source or groups of x-ray sources from the plurality of x-ray sources 120 and to provide them with activation signals. In certain implementations where electron focusing means (not shown) are used in the x-ray sources, the x-ray source controller 160 may be configurable to control and alter the working of the electron focusing means.

Each of the plurality of x-ray detectors 130 is configured to generate a signal that is indicative of the energy and/or number of x-rays that fall on the x-ray detector. In certain implementations, the x-ray detector controller 170 may activate only a selected group of x-ray detectors from the plurality of x-ray detectors 130. By activating only a selective group of x-ray detectors, detection of scattered or stray x-rays by some of the x-ray detectors is reduced. Conversely, the contribution of scattered radiation can be evaluated by activating (only) those detectors that can receive only scattered radiation from the operating sources. A similar procedure could also be used to improve the possibilities for incoherent scatter imaging and multi-modality set-ups using e.g. transmission and scatter tomography. The detector acquisition circuitry 180 is configured to receive the signals from each of the plurality of x-ray detectors 130 via the x-ray detector controller 170 and provide it to the imaging workstation 190 in order to generate an image 195, which may be a 3D image, an image that is decomposed in different materials that constitute the object under investigation or an image from an optimal viewing angle.

Choices of detector materials could be made based on imaging requirements. For example, when increased spatial resolution is required, direct conversion materials such as amorphous selenium, lead oxide, lead iodide, mercury iodide or cadmium zinc telluride (CZT) may be used. In an alternate embodiment where there is a requirement for better temporal behavior that results in faster acquisition, indirect conversion may be employed. In this arrangement, scintillators may be employed in conjunction with photodiodes. Examples of scintillator materials include cesium iodide with thallium, sodium iodide, cadmium tungstate, gadolinium oxysulfide and other known materials. In certain other implementations, photon counting detectors, such as those that are CZT based, and spectrally resolving detectors, such as those used in PET and SPECT systems may also be employed. Either counting mode or integrating mode (summing up the measured x-ray flux during the signal integration time) can be used. Counting and integrating operation can also be combined. Furthermore, x-ray detectors having different energy selectivity and x-ray sources that operate at different kVp may be employed to provide instantaneous images of soft tissue or bone of moving joints etc.

While in the presently embodied imaging apparatus, the x-ray source controller 160, the x-ray detector controller 170, and the data acquisition circuitry 180 are illustrated as being located outside the imaging workstation 190, it should be particularly noted that in certain implementations, some or all of them may be located within the imaging workstation 190. In such a case, the imaging workstation 190 may be arranged to provide some or all of the functionality as desired. Such an arrangement should be construed as being within the scope of the invention as described herein.

Figure 2:
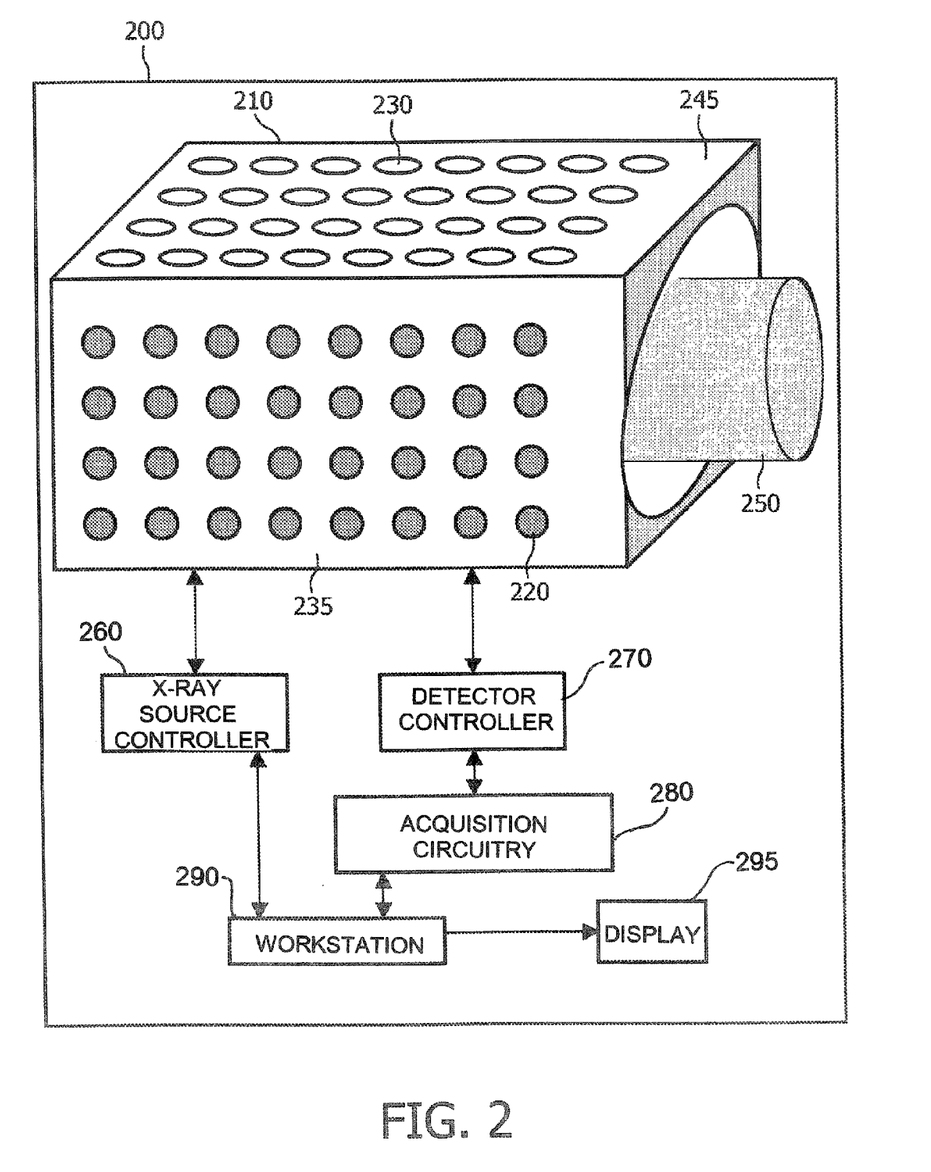
FIG. 2 is a diagrammatical illustration of another exemplary arrangement of an imaging system depicting a plurality of x-ray sources and a plurality of x-ray detectors on a multi-dimensional assembly.

FIG. 2 illustrates another embodiment of an imaging apparatus 200 in accordance with certain aspects of the invention. The imaging apparatus 200 includes a multi-dimensional assembly 210 that further comprises a plurality of x-ray sources 220 and a plurality of x-ray detectors 230. Unlike the imaging system 100 illustrated in FIG. 1, the presently embodied imaging system 200 has plurality of x-ray sources 220 situated away from the plurality of x-ray detectors 230 but on the multi-dimensional assembly 210. In other words, the plurality of x-ray sources 220 are grouped together and arranged on face 235 of the multi-dimensional assembly 210. The plurality of x-ray detectors 230 are grouped together and arranged on another face 245 of the multi-dimensional assembly. While FIG. 2 only illustrates the presence of the x-ray sources 220 and the x-ray detectors 230 on two faces of the multi-dimensional assembly 210, it should not be considered as limiting. Any other arrangement where the plurality of x-ray sources 220 and the plurality of x-ray detectors 230 are grouped amongst themselves and place separate from each other should be considered to be within the scope of the invention as presented.

For example, in a certain implementation, the plurality of x-ray sources 220 may be arranged on two adjacent faces of the multi-dimensional assembly 210 (the arrangement not shown for clarity) while the plurality of x-ray detectors 230 may be arranged on two faces that are opposite to each of the two faces that have the plurality of x-ray sources 220. In a further example, in the case where the multi-dimensional assembly 210 is collapsible in nature, the plurality of x-ray sources 220 and the plurality of x-ray detectors 230 may be arranged in separate groups but where the two groups are arranged next to each other. Moreover, the plurality of x-ray sources 220 and the plurality of x-ray detectors 230 need not be situated in faces that are opposite to each other in all implementations. However, any arrangement of the x-ray sources 220 and the x-ray detectors 230 should be such that x-rays that are emitted by at least one of the x-ray sources that pass through the object 250 can be detected sufficiently to ensure proper acquisition of data to generate a three-dimensional image 295 of the object or part of the object 250 being imaged. Similar to the imaging apparatus 100 illustrated in FIG. 1, the plurality of x-ray sources 220 can be configured to emit x-ray spectra of different mean energies at the same time. The manner in which the generation of x-rays of different energies is achieved is similar to the manner discussed previously in the discussion of FIG. 1.

In another implementation of the invention, x-rays of different energies may be emitted by having x-ray sources 220 grouped together such that each or groups of x-ray sources emits x-ray spectra at a particular mean energy. By having numerous such groups situated on the multi-dimensional assembly 210, it is possible that an object 250 that is to be imaged can be subjected to x-rays of desired energy at any desired region.

Similar to the embodiment described in FIG. 1, the imaging apparatus 200 illustrated in FIG. 2 comprises the x-ray source controller 260, the x-ray detector controller 270, the data acquisition circuitry 280, and the imaging workstation 290. These function in a similar manner as described previously in the description for FIG. 1.

Figure 3:
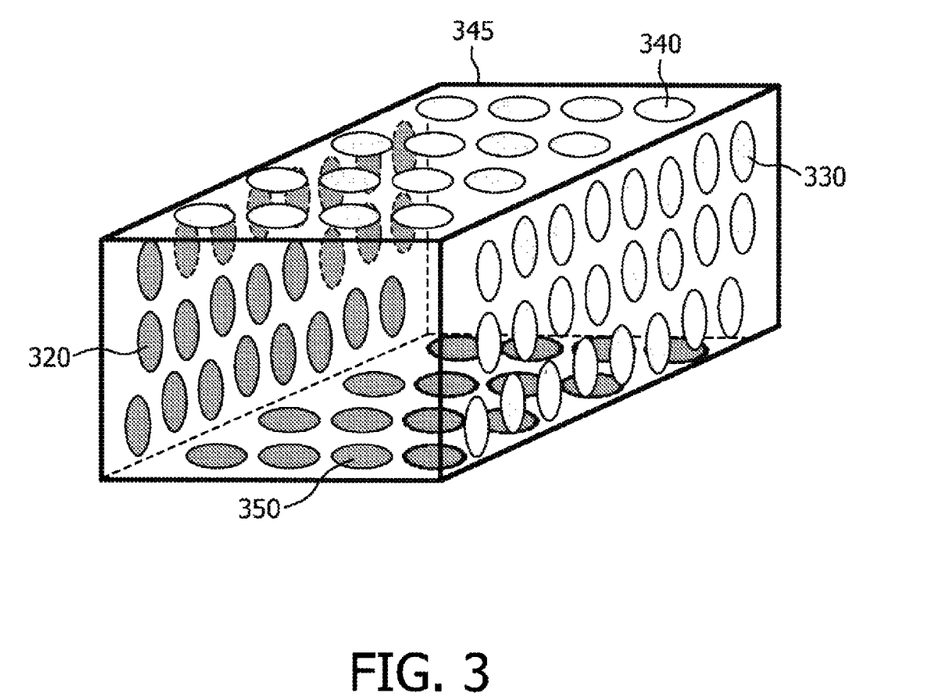
FIG. 3 is a diagrammatical illustration of another exemplary arrangement of the plurality of x-ray sources and the plurality of x-ray detectors on the multi-dimensional assembly.

In a further embodiment of the invention as illustrated in FIG. 1 or FIG. 2, each of the x-ray sources from the plurality of x-ray sources are arranged to emit x-rays for a desired duration of time. For example, the x-ray sources may be activated to emit x-rays in a particular sequence of activation of each of the x-ray sources. The sequence may be series activation, or in other instances, a parallel activation of some or all of the x-ray sources. An advantage of the present embodiment is that it facilitates the extraction of image data of a particular region by increasing the signal to noise ratio of the image signal by reducing the detection of scattered x-rays from a few or the rest of the x-ray sources. It should, further, be noted that during the activation of the x-ray sources in a particular sequence, there would also be one or more x-ray sources that remain inactivated It must be particularly noted that while FIGS. 1 and 2 illustrate two different arrangements of the x-ray sources and the x-ray detectors, it is also possible that other arrangements of the x-ray sources and the x-ray detectors are possible. For example, as stated previously, in a further embodiment as illustrated in FIG. 3, one surface of the multi-dimensional assembly 345 could have the plurality of x-ray sources 320 with an opposing surface of the multi-dimensional assembly would have the plurality of x-ray detectors 330. Furthermore, as illustrated in FIG. 3, the multi-dimensional assembly 345 may also comprise a second set of x-ray sources 340 and x-ray detectors 350 arranged on different but opposing surfaces. Such embodiments should be construed as being within the scope of the invention as recited herein.

Figure 4:
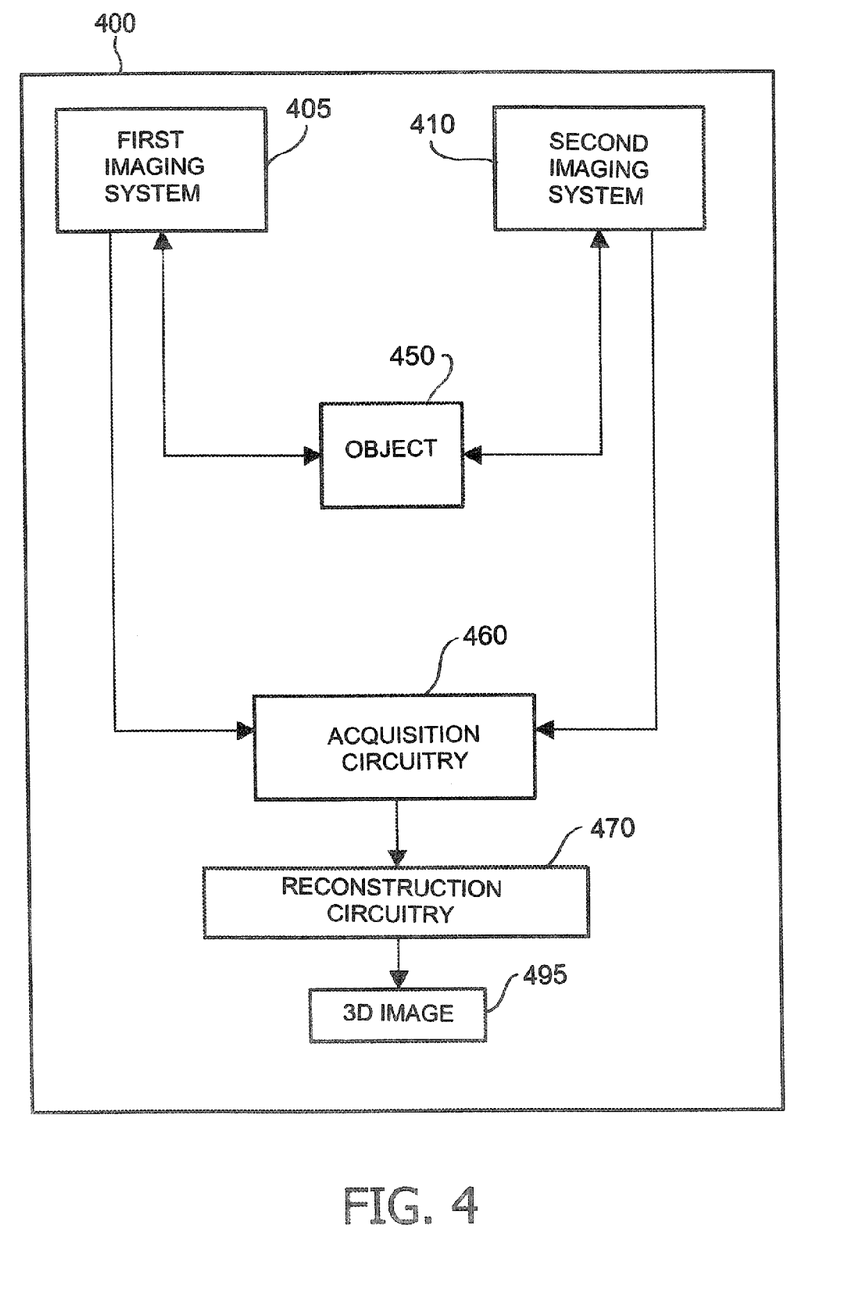
FIG. 4 is a diagrammatical illustration of an exemplary combined modality imaging system.

FIG. 4 illustrates a combined modality imaging system 400 in accordance with yet another aspect of the invention. The combined modality imaging system 400 includes a first imaging system 405, and a second imaging system 410 that are arranged to image an object 450 simultaneously. The combined modality imaging system 400 further includes data acquisition circuitry 460, and image reconstruction circuitry 470 arranged to facilitate generation of a 3D image 495 of the object 450.

In the embodied imaging system 400, it should be noted that imaging systems 405 and 410 are arranged to image and acquire their characteristic image data signals independently from the object 450. For example, the imaging system 405 may provide structural imaging while the imaging system 410 may facilitate functional imaging. The data acquisition circuitry 460 is arranged to acquire the image signals from both the first imaging system 405 and the second imaging system 410 and provide them to the image reconstruction circuitry 470 where an image of the object 450 is reconstructed. As described hereinabove, the generated image could be a 3D image having both structural and functional image content. In certain implementations, the image may comprise two separate images, reconstructed from the first and the second imaging systems 405 and 410 respectively, displayed next to each other on a single or different display apparatus. In certain other implementations, the image 450 may be a single complex image that comprises a superimposition of images reconstructed from the two imaging systems 405 and 410 respectively.

While in the illustrated figure, the two imaging systems 405 and 410 are shown as being separate, it should not be considered limiting. As specified herein, it is quite possible that the respective sources and detectors that are used in both of the imaging systems 405 and 410 may be inter-mingled where necessary. In certain other implementations, imaging systems 405 and 410 may be used to aid one another. For example, the second imaging system 410 may be an optical system that is used to correct for movement artifacts in the image that is generated by the first imaging system.

The first imaging system 405 includes an imaging apparatus as illustrated in FIG. 1 or FIG. 2 or FIG. 3, i.e., the first imaging system 405 comprises at least one of the embodiments as illustrated in FIG. 1 and FIG. 2 and FIG. 3. The second imaging system 410 may include one of the following: an optical imaging system, a positron emission tomography (PET) system, a single positron emission computed tomography (SPECT) system, a computed tomography (CT) system, a thermal imaging system, a magnetic resonance (MR) system or an ultrasound system or combinations.

While the first imaging system 405 operates independent of the second imaging system 410, the imaging systems 405, 410 are configurable to acquire image signals at substantially the same time. For example, while the first imaging system 405 provides structural imaging by generating a 3D image 495, the second imaging system 410 may provide a functional imaging of the same object for the same period of time. By acquiring information through imaging systems that perform structural imaging and functional imaging simultaneously, a better and accurate diagnosis about the existence or the absence of an ailment condition can be arrived at.

In accordance with yet a further aspect of the invention, an exemplary method of operation of an imaging system, example as illustrated in FIG. 1, FIG. 2 or FIG. 3, involves configuring a plurality of x-ray sources to simultaneously emit x-rays at different energies and detecting x-rays that are emitted from the plurality of x-ray sources by an/several x-ray detectors. The manner in which the plurality of x-ray sources may be configured or arranged to emit x-rays at different energies is as discussed previously. In certain embodiments of the invention, as will be appreciated by a person skilled in the art; the method involves advantageously positioning an object to be imaged between an x-ray source and an x-ray detector. It should be noted that by specifying an x-ray source or an x-ray detector does not exclude the possibility of placing the object between any of the plurality of x-ray sources and any of the plurality of x-ray detectors. In certain implementations, the method involves configuring only some of the plurality of x-ray sources to emit x-rays while in certain other implementations, the method involves advantageously configuring each of the x-ray sources from the plurality of x-ray sources to emit x-rays at different points in time. The method further involves the step of generating a visualization of the object based on at the x-rays detected by an x-ray detector. Subsequently, it should be noted that x-rays may also be detected by more than one x-ray detector from the plurality of x-ray detectors and that such detection should be construed as being within the scope of the invention as described herein.

Furthermore, artificial images of the object can be generated. For example, in an exemplary use of the present technique for navigating a catheter through a blood vessel, the optimal viewing angle near a bifurcation or at a curved vessel can be calculated and the imaging system 100 could automatically switch to this viewpoint. In implementations where a model of the blood vessel or other structures of interest (e.g. based on pre-interventional CT or 3D rotational x-ray imaging) is already available, artificial views from 3 or more real views may be generated.

The order in the described embodiments of the method of the current invention is not mandatory, a person skilled in the art may change the order of steps or perform steps concurrently using threading models, multi-processor systems or multiple processes without departing from the concept as intended by the current invention.

As will be appreciated by a person skilled in the art, the reconstruction of the image from the various embodiments of the imaging apparatus described herein may be effected by means of a computer readable code consisting of programmed instructions comprised on a computer readable media. The code, for example, may configure the x-ray source controller to emit the x-rays and to construct an initial image based on the detected x-rays. Code may also be used to analyze the constructed initial image, obtain user inputs and alter the energy of x-rays emitted from the plurality of x-ray sources and generate an optimized image that provides a higher resolution and/or contrast of the imaged portion. In further embodiments, code may also be used in an imaging system comprising the imaging apparatus to implement the above described functions in addition to combining the optimized image with another image generated by a second imaging apparatus, such as those generated from a PET system, a SPECT system, an ultrasound system, and optical system etc. Such code may be a series of sequential or parallel instructions implementing various functions in the imaging system. As will be known to a skilled person, the code may be comprised on a magnetic media, or an optical media and may be in the form of machine-readable instructions or intermediate instructions that require a further compilation to convert the code into the machine-readable form.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging apparatus comprising:
   a multi-dimensional assembly having a plurality of x-ray sources and a plurality of x-ray detectors distributed thereon, the plurality of x-ray sources each being individually addressable to be controlled individually to emit an x-ray spectrum at an individually controllable mean energy, the plurality of x-ray detectors each being arranged to detect the x-ray spectra emitted from one or more of the plurality of x-ray sources, a workstation which processes signals from the plurality of x-ray detectors to generate a visualization, and an x-ray source controller which addresses the plurality of x-ray sources and controls the mean spectrum energy of each of the plurality of x-ray sources based on properties of the visualization.

2. The imaging apparatus as claimed in claim 1, wherein the multi-dimensional assembly, the plurality of x-ray sources and the plurality of x-ray detectors are stationary.

3. The imaging apparatus as claimed in claim 1, wherein the plurality of x-ray sources are distributed amongst the plurality of x-ray detectors on a surface of the multi-dimensional assembly.

4. The imaging apparatus as claimed in claim 3, wherein the plurality of x-ray sources are arranged on at least a first surface of the multi-dimensional assembly and the plurality of x-ray detectors are arranged on at least a second surface of the multi-dimensional assembly, the first surface being different from the second surface.

5. The imaging apparatus as claimed in claim 1, wherein each x-ray source comprises a cold cathode x-ray source.

6. The imaging apparatus as claimed in claim 5, wherein the cold cathode x-ray source comprises one of a carbon nanotube, carbon tip, carbon composite tip, metal tip, semiconductor tip, a pyroelectric material or a ferroelectric material or combinations thereof.

7. The imaging apparatus as claimed in claim 1, wherein the imaging apparatus is arranged to image an object at rest when in operation.

8. The imaging apparatus as claimed in claim 1, wherein each of the plurality of x-ray detectors are configurable for detecting x-rays at different mean energies.

9. The imaging apparatus as claimed in claim 1, wherein an object with directionally dependent x-ray attenuation characteristics that are different in some directions than in other directions is disposed between the x-ray sources and the x-ray detectors and the x-ray sources are configured to control the energy spectra in accordance with the directionally dependent x-ray attenuation characteristics of the object.

10. A combined modality imaging system comprising:
a first imaging system comprising the imaging apparatus as claimed in claim 1; and
a functional imaging system;
wherein the first imaging system and the functional imaging system are arranged to image a common region of an object.

11. The combined modality system as claimed in claim 10, wherein the functional imaging system comprises an optical imaging system, a magnetic resonance (MR) imaging system or a positron emission tomography (PET) system, or a single positron emission computed tomography system (SPECT), or a computed tomography (CT) system, a thermal imaging system or an ultrasound system.

12. A method of operation of an imaging system, comprising:
configuring a plurality of x-ray sources to simultaneously emit x-ray spectra at two or more different mean energies;
positioning an object to be imaged between the plurality of x-ray sources and at least one x-ray detector;
detecting the x-ray spectra emitted from the plurality of x-ray sources;
generating a visualization of the object based on x-rays detected by the at least one x-ray detector;
analyzing the generated visualization;
altering one or more image acquisition parameters based on the analysis of the generated visualization to generate an improved image; and
altering projection angles of one or more x-ray sources from the plurality of the x-ray sources to improve a resolution and/or contrast of the visualization.

13. A method of operating an imaging system comprising:
configuring a plurality of x-ray sources to simultaneously emit x-ray spectra at two or more different mean energies;
positioning an object to be imaged between the plurality of x-ray sources and at least one x-ray detector;
detecting the x-ray spectra emitted from the plurality of x-ray sources;
generating a visualization of the object based on x-rays detected by the at least one x-ray detector;
analyzing the generated visualization; and
altering one or more image acquisition parameters based on the analysis of the generated visualization to generate an improved image, including altering an energy of the x-ray spectrum emitted by the plurality of x-ray sources individually and differently.

14. The method of operation of the imaging system as claimed in claim 13, wherein the step of altering the one or more image acquisition parameters comprises:
altering at least one of a duration of x-ray emission, the mean energy of x-rays emitted from one or more x-ray sources from the plurality of x-ray sources, a sequence of x-ray emission from the one or more x-ray sources from the plurality of x-ray sources or combinations thereof until at least one parameter of the visualization is improved.

15. A method of operating an imaging system comprising:
(a) controlling a plurality of individually controllable x-ray sources to irradiate a plurality of x-ray detectors through an object to be imaged;
(b) processing signals from the plurality of x-ray detectors to generate an image of the object;
(c) analyzing the image for at least one of resolution and contrast; and
(d) individually and differently adjusting an energy spectrum emitted by at least some of the plurality of x-ray sources to adjust an energy of x-rays emitted by at least some of the plurality of x-ray sources to improve at least one of the resolution and the contrast of the image.

16. The method as claimed in claim 15, wherein the method further includes:
repeating steps (b)-(d) until at least one of the resolution and the contrast is optimized.

17. A tangible non-transitory computer readable medium carrying computer code which controls one or more computers to perform the method as claimed in claim 15.

18. An imaging system comprising:
a plurality of individually controllable x-ray sources arranged around in an imaging region configured to receive an object to be imaged, the plurality of x-ray sources being individually controllable to adjust an energy of emitted x-rays;
a plurality of radiation detectors disposed around the imaging region each to receive x-rays emitted by one or more of the plurality of x-ray sources; and
one or more processors programmed to perform the method as claimed in claim 15.

* * * * *